United States Patent [19]

Jones et al.

[11] 4,321,399
[45] Mar. 23, 1982

[54] PREPARATION OF 2-THIOPHENECARBONYL CHLORIDE

[75] Inventors: Stella S. Jones, Voorhees, N.J.; Christine B. Ogston, Philadelphia; Robert L. Webb, West Chester, both of Pa.

[73] Assignee: SmithKline Corporation, Philadelphia, Pa.

[21] Appl. No.: 917,720

[22] Filed: Jun. 21, 1978

[51] Int. Cl.³ .......................................... C07D 333/24
[52] U.S. Cl. .................................................. 549/70
[58] Field of Search .................... 260/332.2 C; 549/70

[56] References Cited
PUBLICATIONS

Rueggeberg et al. "Ind. & Eng. Chem." 38 pp. 624–626.
Rodd "Heterocyclic Compounds" vol. III part A, p. 252.

Primary Examiner—Alan Siegel
Attorney, Agent, or Firm—William H. Edgerton; Richard D. Foggio; Alan D. Lourie

[57] ABSTRACT

Thiophenecarbonyl chloride is produced in good yields by the direct acylation of thiophene in the presence of aluminum chloride with control of temperature and concentration.

7 Claims, No Drawings

PREPARATION OF 2-THIOPHENECARBONYL CHLORIDE

This invention comprises a novel and effective preparation of the commercial chemical, 2-thiophenecarbonyl chloride, by means of the direct chlorocarbonylation of thiophene in the presence of aluminum chloride.

STATEMENT OF THE ART

To our knowledge there is no report in the literature of the preparation of thiophenecarbonyl halides by direct halocarbonylation. G. Kuhnhanss, et al. J. fur Practische Chemie, (4) 275 137 (1956) describes acylation of thiophene with carbamyl chloride or oxalyl chloride, Gattermann, Ber. 1830 13 (1885) reports only formation of dithienylketone. The usual preparation of thiophenecarbonyl halides is by successive formation of the 2-acetyl derivative, the 2-acid then reaction of the acid with thionyl chloride, see, for example, U.S. Pat. No. 3,338,921. Reaction of phosgene or oxalyl chloride with non-heterocyclic aromatic compounds is difficult to stop at the acid chloride stage but gives either the carboxylic acid, the ketone or, more likely, mixtures of the two products. See, for example, S. Patai, The Chemistry of Acyl Halides, Interscience 1972 pages 57-63, G. Olah, Friedel-Crafts and Related Reactions, Interscience Vol. III 1257 (1972) or W. Rueggeberg et al. Ind. and Eng. Chem. 38 624 (1946). In addition to being a general commercially important intermediate, thiophenecarbonyl chloride is used to prepare the diuretic, ticrynafen, U.S. Pat. No. 3,758,506.

DESCRIPTION OF THE INVENTION

We have now unexpectedly discovered that under certain conditions thiophene can be directly acylated to give thiophenecarbonyl chloride (thenoyl chloride) in good yields.

The reaction is run using substantially equimolar quantities of thiophene, phosgene and aluminum chloride. The critical aluminum chloride catalyst however may be used in excess without lowering yields such as in 5-10% excess. A common organic solvent is used which is chemically inert to the reactants, which is of a polarity that the phosgenealuminum chloride acylation complex (see G. Olah above) is maintained intact and which is liquid at the temperature of the reaction. Such solvents may be selected from the common halogenated solvents for example chloroform, carbon tetrachloride, methylene chloride, tetrachloroethylene, toluene, nitrobenzene, chlorobenzene, dichlorobenzene, o-xylene, cymene, carbon disulfide, dimethylsulfoxide or liquid phosgene. Mixtures of the common organic solvents mentioned may also be used.

The temperature of the reaction has been found to be critical to obtaining a favorable ratio of acid chloride to ketone. Normally the temperature is selected from the range of about 0° C. down to just above the freezing point of the reaction mixture. Advantageously a temperature is selected from about −15° to −25° C. Some acid chloride is obtained at higher temperatures such as at room temperature but the tendency of the acid chloride to react with thiophene to form thiophene ketone makes the reaction less attractive at relatively high temperatures. The reaction occurs as soon as the thiophene is contacted with the catalyst-phosgene mixture. The reaction mixture is therefore worked up so that continued contact is minimal.

Another factor which we have found that should be controlled to insure a high yield of the desired thiophenecarbonyl chloride is the state of concentration of the reactants, especially the thiophene, in the solvent. Higher concentrations of thiophene yield higher quantities of the ketone by-product. In practice we have found that from 5-10% of the thiophene per reaction mixture gives good yields. Substantially more of the thiophene increases the ratio of ketone. For example 15-20% of thiophene gives relatively more ketone.

Because of the easy, almost instantaneous, reaction of the ingredients, the temperature effect and the dilution factor, the process of this invention may advantageously be carried out in a continuous stream reaction or a flow through reactor although we have not to date so carried out the reaction in this manner.

The Lewis acid catalyst, aluminum chloride, has also proved to be specific to date in our hands. Zinc chloride, titanium tetrachloride, boron trifluoride etherate, stannic chloride, iodine and no catalyst gave little acid chloride. Ferric chloride at 3 hours and −20° C. gave some product.

Any convenient isolation procedure well known in the art can be used to isolate the desired thiophene carbonyl chloride. We have found that the use of neutral, basic or weakly aqueous media tends to yield undesirable proportions of thiophenecarboxylic acid. Strongly acid media such as 25% hydrochloric acid or various aqueous acid solutions of pH<1 are therefore advantageously used in the work-up procedure. Alternatively the product can be used in situ by methods known to the art.

The following are intended to exemplify this invention and to describe the best method known at this time for carrying out this invention. All temperature are on the Centigrade scale.

EXAMPLE 1

A solution of 0.01 mole (990 mg) of phosgene in 16 ml of methylene chloride was cooled in dry ice/carbon tetrachloride to −20°. To this was added 1.34 g (0.01 mole) of anhydrous aluminum chloride to form a grey slurry. A solution of 0.8 ml (0.01 mole) of thiophene in 8 ml of methylene chloride was slowly added (addn time ~ 20 min). Immediately after the addition the mixture was poured into iced 25% hydrochloric acid with stirring, the color changed from red to yellow and the organic phase was separated. The aqueous acid was extracted twice with methylene chloride and the organic phases combined then dried over anhydrous magnesium sulfate. Gas liquid chromatography (on a 6' column of 3% dimethylsilicone packing (OV-101) initial temp 70° final temp 200° programmed at 10°/min) shows little or no thiophene and 96 to 100% acid chloride (less than 5% of ketone).

The acid chloride may be distilled at 85° C. at aspirator pressure to give water white liquid analyzed to contain no 3-isomer (99.8% acid chloride).

These catalysts were also tried on same scale under same reaction conditions. No reaction occurred.

.ZnCl$_2$ .SnCl$_4$
.TiCl$_4$ .no catalyst
.BF$_3$.OE+2 .I$_2$ (both cat, and equimole)

With equimolar amounts of FeCl$_3$ after 3 hours at −20° C. a small amount of product was detected by gas liquid chromatography.

What is claimed is:

1. The method of producing 2-thiophenecarbonyl chloride comprising reacting substantially equimolar quantities of thiophene and phosgene in the presence of aluminum chloride in a chemically inert organic solvent which is capable of maintaining intact the phosgenealuminum complex and which is liquid at the reaction temperature at a temperature selected from the range of from about 0° down to the freezing point of said solvent.

2. The method of claim 1 in which a halogenated organic solvent is present.

3. The method of claim 2 in which the solvent is methylene chloride.

4. The method of claims 1, 2 or 3 in which the temperature is selected from the range of −15° to −25° C.

5. The method of claims 1, 2 or 3 in which the concentration of thiophene is less than 10% by weight of said solvent.

6. The method of claims 1, 2 or 3 in which the reaction mixture is worked up using a quench of strong aqueous acid.

7. The method of claim 1 in which the temperature is selected from the range of −15° to −25°, methylene chloride is used as the solvent medium, and the concentration of thiophene to solvent medium is less than about 10%.

* * * * *